US012766117B2

(12) United States Patent
Chu et al.

(10) Patent No.: US 12,766,117 B2
(45) Date of Patent: Oct. 20, 2026

(54) PREPARATION METHOD AND USE OF LIPOSOME ENCAPSULATING POLYPEPTIDE, SUBEROYLANILIDE HYDROXAMIC ACID (SAHA), AND VITAMIN A

(71) Applicant: UNION HOSPITAL, TONGJI MEDICAL COLLEGE, HUAZHONG UNI. OF SCIENCE AND TECH., Wuhan (CN)

(72) Inventors: Huikuan Chu, Wuhan (CN); Dongyuan Wang, Wuhan (CN); Wenkang Gao, Wuhan (CN); Ling Yang, Wuhan (CN); Yue Chen, Wuhan (CN); Yuanqing Zhu, Wuhan (CN); Hang Yuan, Wuhan (CN); Zilu Cheng, Wuhan (CN); Jiake Che, Wuhan (CN); Yupin Tan, Wuhan (CN); Shengqi Yan, Wuhan (CN); Wei Li, Wuhan (CN); Zexuan Li, Wuhan (CN); Ao Liu, Wuhan (CN)

(73) Assignee: UNION HOSPITAL, TONGJI MEDICAL COLLEGE, HUAZHONG UNI. OF SCIENCE AND TECH., Wuhan (CN)

( * ) Notice: Subject to any disclaimer, the term of this patent is extended or adjusted under 35 U.S.C. 154(b) by 138 days.

(21) Appl. No.: 18/882,995

(22) Filed: Sep. 12, 2024

(65) Prior Publication Data

US 2025/0161244 A1 May 22, 2025

(30) Foreign Application Priority Data

Nov. 20, 2023 (CN) ......................... 202311558561.9

(51) Int. Cl.

*A61K 31/167* (2006.01)
*A61K 9/127* (2025.01)
*A61K 9/1277* (2025.01)
*A61K 31/07* (2006.01)
*A61P 1/16* (2006.01)

(52) U.S. Cl.

CPC .......... *A61K 31/167* (2013.01); *A61K 9/1277* (2013.01); *A61K 31/07* (2013.01); *A61P 1/16* (2018.01)

(58) Field of Classification Search

None

See application file for complete search history.

(56) References Cited

U.S. PATENT DOCUMENTS

2021/0353715 A1* 11/2021 John .................. C07K 14/4726

OTHER PUBLICATIONS

Lombardo et al. (Pharmaceutics 2022, 14, 543, 1-49 (Year: 2022).*
Ozel et al. (Cell Biochemistry and Biophysics 2021; 79:349-357) (Year: 2021).*
Wang et al. (Cell Death Discovery (2022) 8:411) (Year: 2022).*
Sachaniya et al. (International Journal of Nanomedicine, 2018: 13 51-53) (Year: 2018).*

* cited by examiner

*Primary Examiner* — Anna R Falkowitz
(74) *Attorney, Agent, or Firm* — JEEN IP LAW, LLC

(57) ABSTRACT

A preparation method of a liposome encapsulating a polypeptide, suberoylanilide hydroxamic acid (SAHA), and vitamin A is provided, including the following steps: dissolving choline, cholesterol, an anti-angiogenic lytic peptide, the SAHA, and the vitamin A in a chloroform-methanol solution and mixing evenly, and subjecting an obtained mixed solution to spin drying under reduced pressure to form a film; and subjecting the film to hydration with a phosphate-buffered saline (PBS) solution or $ddH_2O$ to obtain the liposome. Use of the preparation method is further provided, where a liposome prepared by the preparation method is used as a drug for treating hepatic fibrosis. An “anti-hepatic fibrosis drug” is combined with “liver-targeted vitamin A” to construct a “target liposome encapsulating the anti-hepatic fibrosis drug”.

7 Claims, 8 Drawing Sheets

Structural schematic diagram of a liposome

Anti-angiogenic lytic peptide

PREPARATION METHOD AND USE OF LIPOSOME ENCAPSULATING POLYPEPTIDE, SUBEROYLANILIDE HYDROXAMIC ACID (SAHA), AND VITAMIN A

CROSS REFERENCE TO RELATED APPLICATION

This patent application claims the benefit and priority of Chinese Patent Application No. 202311558561.9 filed with the China National Intellectual Property Administration on Nov. 20, 2023, the disclosure of which is incorporated by reference herein in its entirety as part of the present application.

TECHNICAL FIELD

The present disclosure relates to the technical field of biomedicine, and in particular to a preparation method and use of a liposome encapsulating a polypeptide, suberoylanilide hydroxamic acid (SAHA), and vitamin A.

BACKGROUND

Hepatic fibrosis refers to a chronic lesion mainly caused by recurrent hepatitis characterized by diffuse and excessive deposition of extracellular matrix (especially collagen) inside the liver. When lesions continue to progress after hepatic fibrosis and lead to the destruction of hepatic lobule structure, fibrous scars formation, nodule regeneration, and insufficient blood supply, then they develop into cirrhosis. Hepatic fibrosis is a reversible process, however, most cirrhosis, is irreversible. Advanced cirrhosis and related complications are the main causes of death in patients with chronic hepatic disease. Therefore, it is an important link in reducing the mortality rate of patients with chronic hepatic diseases and preventing the further progression by inhibiting the synthesis of extracellular matrix or promoting the degradation of extracellular matrix to reverse the established hepatic fibrosis. However, due to the complex pathogenesis, currently, there is still a lack of efficient and specific treatments for hepatic fibrosis.

I. Causes of Hepatic Fibrosis

It is currently believed that activated hepatic stellate cells (HSCs), bone marrow-derived cells, portal fibroblasts, and epithelial-to-mesenchymal transition (EMT) are the main sources of myofibroblasts. "Continuous activation of HSCs" is a key link in the development of hepatic fibrosis as well as a hot topic and difficulty in research in recent years' studies. Transforming growth factor-beta (TGF-β), platelet-derived growth factor (PDGF), vascular endothelial growth factor (VEGF), and connective tissue growth factor (CTGF) induce the production of extracellular matrix by promoting the proliferation and migration ability of HSCs and continuously promote the fibrogenic response to accelerate the progression of hepatic fibrosis. In addition, epigenetic regulation of HSCs (miRNA, histone modification, and DNA methylation) and receptors (such as Toll-like receptors, farnesoid X receptors, hepatic X receptors, and peroxisome proliferator-activated receptors)-mediated HSC regulation are also involved in the development and progression of hepatic fibrosis. Moreover, factors such as environment, diet, host genetics, and gut microbiota may also affect the progression of hepatic fibrosis. In conclusion, the specific pathogenesis of hepatic fibrosis remains to be studied.

II. Treatment of Hepatic Fibrosis

Clinical treatment to patients with hepatic fibrosis or cirrhosis mainly includes etiological treatment, fibrosis treatment, and complication treatment, with the etiological treatment as a basis. However, the etiological treatment alone cannot completely block the progression of hepatic fibrosis. For example, patients with alcohol-related hepatic disease and chronic hepatitis B may still develop into cirrhosis or even liver cancer after abstaining from alcohol or inhibiting hepatitis B virus replication. As a result, it is necessary to fight hepatic fibrosis while treating the etiology. Currently, there is no drug for the treatment of hepatic fibrosis that has been verified by clinical trials and approved by relevant departments. In the present disclosure, drugs that may have therapeutic potential are summarized based on the existing literature as follows:

(I) Anti-fibrotic Effects of Histone Deacetylase (HDAC)-Targeted Inhibitors

Studies have shown that epigenetic modifications in patients with hepatic fibrosis are different from those in healthy people. Histone acetylation, the most extensively and deeply studied epigenetic regulatory process, is mainly regulated by HDAC and histone acetyltransferase. The HDAC is a family of enzymes that can promote the deacetylation of protein lysine residues, and plays an extremely important role in physiological and pathological processes such as cell cycle, apoptosis, and autophagy. Vorinostat (suberoylanilide hydroxamic acid, SAHA) is a broad-spectrum HDAC inhibitor which can inhibit HSC activity through the TGF-β1 pathway, and can also inhibit PDGF-induced HSC proliferation and promote HSC apoptosis by regulating the cell cycle. In addition, the SAHA also plays a role in regulating epithelial-mesenchymal transition. HDAC inhibitors represented by SAHA are helpful in treating hepatic fibrosis. However, since the histone acetylation is also important for the normal physiological functions of other tissue cells, broad-spectrum inhibition may have adverse effects on the body. Accordingly, further research and development is needed for drugs targeting the hepatic fibrosis, especially HSCs.

(II) Vitamin A

Vitamin A is a fat-soluble vitamin. In vitro and in vivo experiments have demonstrated that a unique cross-linked nanopolymer modified with the vitamin A effectively inhibits the activation of HSCs and the expression of their profibrotic proteins by delivering PDGFR-β siRNA to the HSCs. Another study has found that a nanoparticle preparation of polyethylene glycol-polycaprolactone polymer modified by vitamin A derivatives delivering camptothecin (a hydrophobic drug against HIF-1) micelles can target liver HSCs and significantly weaken hepatic fibrosis in mice, thus effectively improving damaged liver structure and function. The above studies show that nano-drugs loading with the vitamin A exhibit desirable liver and HSC targeting properties and are excellent guides for the development of liver-targeted drugs.

(III) Anti-Angiogenic Lytic Peptide

Hepatic fibrosis is generally accompanied by angiogenesis, which in turn aggravates the hepatic fibrosis. In the early stage of hepatic fibrosis, collagen fibers remodeled by hepatic sinusoidal capillary angiogenesis can act as mechanical force transduction mediators to activate HSCs. Other studies have pointed out that hepatic sinusoidal capillary angiogenesis promotes hepatic fibrosis, while portal vein angiogenesis inhibits hepatic fibrosis. Simultaneously inhibiting hepatic sinusoidal capillary angiogenesis and promoting portal vein angiogenesis is more effective in treating hepatic fibrosis.

III. Liposome for Drug Delivery

Liposomes were first discovered by British scientists in the 1960s. The liposomes are in closed spherical structures of a bilayer (monolayer) and/or concentric multiple bilayer (multilayers) closed central water cavities. Because of their structure similar to the plasma membrane of living organisms, liposomes show high biocompatibility and are thus called "artificial biomembranes", making them highly-potential drug delivery systems.

Liposome drug delivery has the following advantages: (1) a wide range of drug delivery: hydrophilic drugs can be encapsulated in the aqueous phase environment inside liposomes, lipophilic drugs can be dispersed in the lipid bilayer, and amphiphilic substances can be positioned on the phospholipids at an interface between the aqueous phase and the membrane. (2) Targeting ability: a bilayer surface formed by amphiphilic phospholipids can be structurally modified with ligands or other functional groups through physical or chemical means. This process makes liposomes tissue-targeted, prolongs the effective retention time of liposomes at the lesion site, and can even achieve efficient targeted drug delivery. In addition, by changing charge on the bilayer surface, the liposomes can be used for the encapsulation and delivery of DNA and RNA drugs. (3) Desirable biocompatibility: since having a structure similar to that of biomembranes, liposomes show excellent cell affinity and tissue compatibility, can be adsorbed around target cells for a long time, and can even directly enter cells to release drugs through lysosomal digestion. (4) High bioavailability: since phospholipids are also a main component of cell membranes, liposomes are non-toxic and do not cause immune damage after being injected into the body. (5) Improving drug stability: liposomes provide a protective barrier for their carried drugs, thereby preventing dilution of the drugs by body fluids and decomposition and destruction of the drugs by hydrolases. (6) Reducing drug toxicity: the accumulation of drugs in tissues and organs after liposome encapsulation is much lower than that after conventional administration. Therefore, drugs that are harmful to tissues and organs can be prepared into the liposomes to reduce toxicity. In summary, the liposomes, with their unique properties, make it possible for many drugs to treat diseases.

In summary, combined with the above analysis in the present disclosure, "drugs with anti-hepatic fibrosis (HDAC inhibitor-SAHA and anti-angiogenic lytic peptide)" and "liver-targeted vitamin A" can be combined to construct "targeted liposomes encapsulating anti-hepatic fibrosis drugs". These targeted liposomes can be used to accurately and specifically bring anti-hepatic fibrosis drugs into the liver to effectively exert their effects, thereby achieving efficient and specific treatment of the hepatic fibrosis.

SUMMARY

The technical problems to be solved by the present disclosure are to provide a preparation method and use of a liposome encapsulating a polypeptide, SAHA, and vitamin A. The liposome can specifically and accurately bring anti-hepatic fibrosis drugs into the liver to effectively exert their effects, thereby achieving efficient and specific treatment of hepatic fibrosis.

The present disclosure adopts the following technical solutions to solve the above technical problems:

The present disclosure provides a preparation method of a liposome encapsulating a polypeptide, SAHA, and vitamin A, including the following steps:

S1, dissolving choline, cholesterol, lytic peptide, SAHA, and vitamin A in a chloroform-methanol solution and mixing evenly, and subjecting an obtained mixed solution to spin drying under reduced pressure to form a film; and S2, subjecting the film to hydration with a phosphate-buffered saline (PBS) solution or $ddH_2O$ to obtain the liposome.

In some embodiments, chloroform and methanol in the chloroform-methanol solution in step S1 are mixed at a volume ratio of 1:1.

In some embodiments, the choline, the cholesterol, the anti-angiogenic lytic peptide, the SAHA, and the vitamin A in step S1 are mixed at a molar ratio of 10:8:1:2:2.

In some embodiments, the hydration in step S2 specifically includes: adding the PBS solution or the $ddH_2O$ into a container containing the film, and then placing the container in an ultrasonicator at 60° C. to allow ultrasonication until a suspension uniformly dispersed is formed to the naked eyes.

In some embodiments, the ultrasonication is conducted at a frequency of 53 Hz and a power of 90% for 30 min.

In some embodiments, the container is vortexed in a vortexer for 30 s after every 10 min of the ultrasonication; the above operations are repeated alternately until a uniformly dispersed suspension is formed to the naked eyes.

In some embodiments, the liposome is used to alleviate hepatitis and hepatic fibrosis.

The present disclosure further provides use of the preparation method of a liposome encapsulating a polypeptide, SAHA, and vitamin A, where a liposome prepared by the preparation method is used as a drug for treating hepatic fibrosis.

The advantages of the present disclosure compared to the prior art are: an "anti-hepatic fibrosis drug (SAHA and anti-angiogenic lytic peptide)" is combined with "liver-targeted vitamin A" to construct a "targeting liposome encapsulating the anti-hepatic fibrosis drug". On one hand, the drug can reach liver quickly, accurately, and safely, facilitating a concentrated and high-concentration drug effect; on the other hand, based on a synergistic effect of components such as SAHA and anti-angiogenic lytic peptide QR-KLU, there is a highly effective effect in alleviating and treating hepatitis and hepatic fibrosis.

BRIEF DESCRIPTION OF THE DRAWINGS

FIG. 1A shows the structure of the liposome; and FIG. 1B shows the design of the anti-angiogenic lytic peptide QR-KLU);

FIG. 4A shows a ratio of liver weight to body weight of each group of mice; FIG. 4B shows a level of serum alanine aminotransferase (ALT) of each group of mice and FIG. 4C shows a level of aspartate aminotransferase (AST) of each group of mice; a difference between the two groups is analyzed using t-test, *: $p<0.05$, ** $p<0.01$, $p<0.001$, ns: $p>0.05$, indicating that there is no statistically significant difference between the two groups);

FIG. 5A shows the expression of liver IL-1β; FIG. 5B shows the expression of liver TNF-α; and FIG. 5C shows the expression of liver α-SMA; a difference between the two groups is analyzed using t-test, *: $p<0.05$,  $p<0.01$, * $p<0.001$);

DETAILED DESCRIPTION OF THE EMBODIMENTS

The examples of the present disclosure will be described in detail below. The examples are implemented on the premise of the technical solution of the present disclosure, and detailed implementation and specific operation procedures are provided, but the protection scope of the present disclosure is not limited to the following examples. Meanwhile, the reagents and experimental methods used in the following examples and experimental examples are conventional reagents or methods in the art unless otherwise specified and will not be described in detail.

Example 1

Figure 1A:
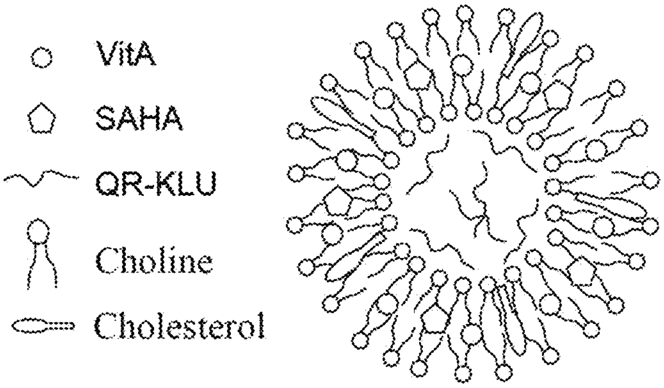
FIG. 1A-1B show schematic diagrams of the structures of the liposome and the anti-angiogenic lytic peptide QR-KLU in Example 1 (where

In this example, a liposome encapsulating a polypeptide, SAHA, and vitamin A having a structure as shown in FIG. 1A, was prepared by the following steps:

S1, choline, cholesterol, an anti-angiogenic lytic peptide, the SAHA as an HDAC inhibitor, and the vitamin A were dissolved in a chloroform-methanol solution (chloroform and methanol mixed at a volume ratio of 1:1), respectively and mixed evenly at a molar ratio of 10:8:1:2:2, and an obtained mixed solution was placed in a round-bottom flask and subjected to spin drying under reduced pressure to form a film.

S2, the film was subjected to hydration with a 0.01 M PBS solution (pH=7.4) or $ddH_2O$, i.e., including: a certain volume of the PBS solution or $ddH_2O$ was added into a container containing the film, and then the container was placed in an ultrasonicator (53 Hz, 90% power) at 60° C. to allow ultrasonication for 30 min, where after every 10 min of the ultrasonication, the container was vortexed in a vortexer for 30 s, and the above operations were repeated until a suspension uniformly dispersed was formed to the naked eyes, thereby obtaining the liposome.

Figure 1B:
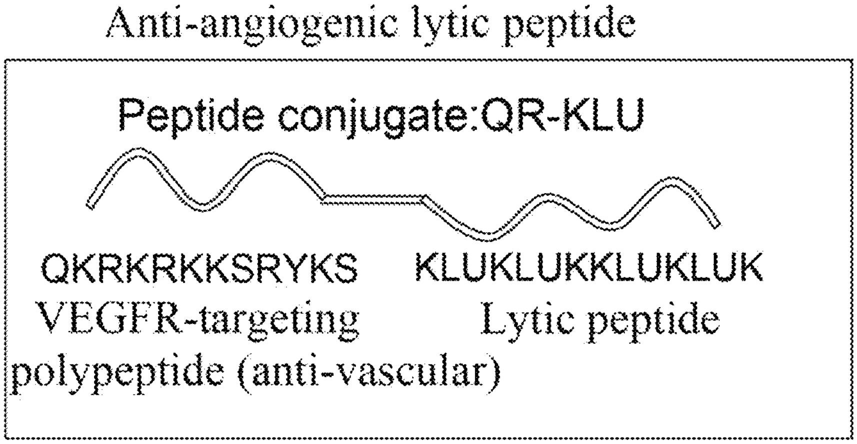

In this example, the QR-KLU was specifically adopted as an anti-angiogenic lytic peptide as shown in FIG. 1B, which was a lytic peptide conjugate QR-KLU product targeting VEGFR in the Patent with an authorization announcement number of CN114213546 B "Lytic peptide conjugate targeting VEGFR and use thereof".

Example 2

In this example, the liposome encapsulating a polypeptide, SAHA, and vitamin A prepared in Example 1 was characterized.

The liposome suspension prepared in Example 1 was centrifuged in an ultracentrifuge (10,000 rpm, 30 min) to fully precipitate the liposome; an appropriate amount of the precipitate was resuspended in 1 mL to 2 mL of PBS solution, shaken evenly, and then a particle size thereof was measured using a particle size analyzer.

Figure 2:
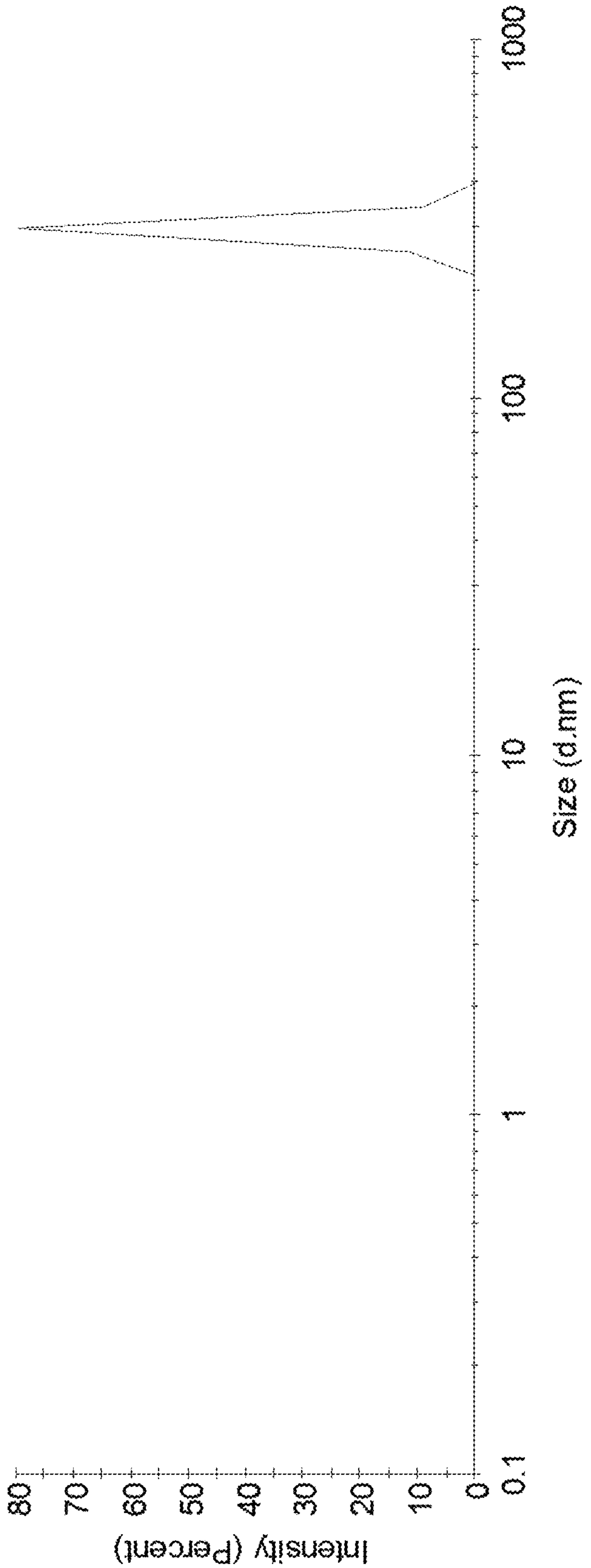
FIG. 2 shows the particle size distribution of the liposome prepared in Example 2 of the present disclosure.

As shown in FIG. 2, the liposome had an average particle size of 294 nm, which was consistent with a liposome nanoparticle size reported in the literature, proving that the liposome was successfully prepared.

Example 3

In this example, an effect of the liposome encapsulating a polypeptide, SAHA, and vitamin A prepared in Example 1 was verified.

The liposome suspension prepared in Example 1 was centrifuged in an ultracentrifuge (10,000 rpm, 30 min) to fully precipitate the liposome; followed which a supernatant was discarded, and the remaining liposome was resuspended in a cell medium (a high-glucose Deme medium) for subsequent experiments.

I. In Vitro Experiment

1. Experimental purpose: the drug and its various components were added into the cell medium, respectively to explore whether there was an inhibitory effect on the proliferation of HSCs. The continuous activation of HSC was a key link in the development of hepatic fibrosis, and inhibiting the proliferation or activation of HSC was an important means to treat hepatic fibrosis.

2. Experimental method: a "CCK8 experiment" was conducted to verify the effectiveness of the liposome drug disclosed in the present disclosure on liver fibroblasts, specifically as follows:

LX-2 cells (human HSCs) were inoculated in a 96-well plate at a density of 8,000 cells/well. After 24 h of culture, different components of the drug were respectively incubated with the cells for 48 h, and then a CCK-8 reagent was used for cytotoxicity detection. The components were SAHA (0 μM, 2.5 μM, and 5 μM), anti-angiogenic lytic peptide QR-KLU (0 μM, 2.5 μM, and 5 μM), VA (0 μM, 2.5 μM, and 5 μM), as well as drug-loaded liposomes SAHA@liposome (0 μM, 2.5 μM, and 5 μM), QR-KLU@liposome (0 μM, 2.5 μM, and 5 μM), VA@liposome (0 μM, 2.5 μM, and 5 μM), and QR-KLU+SAHA+VA@liposome (QR-KLU:VA:SAHA=1:2:2).

Figure 3:
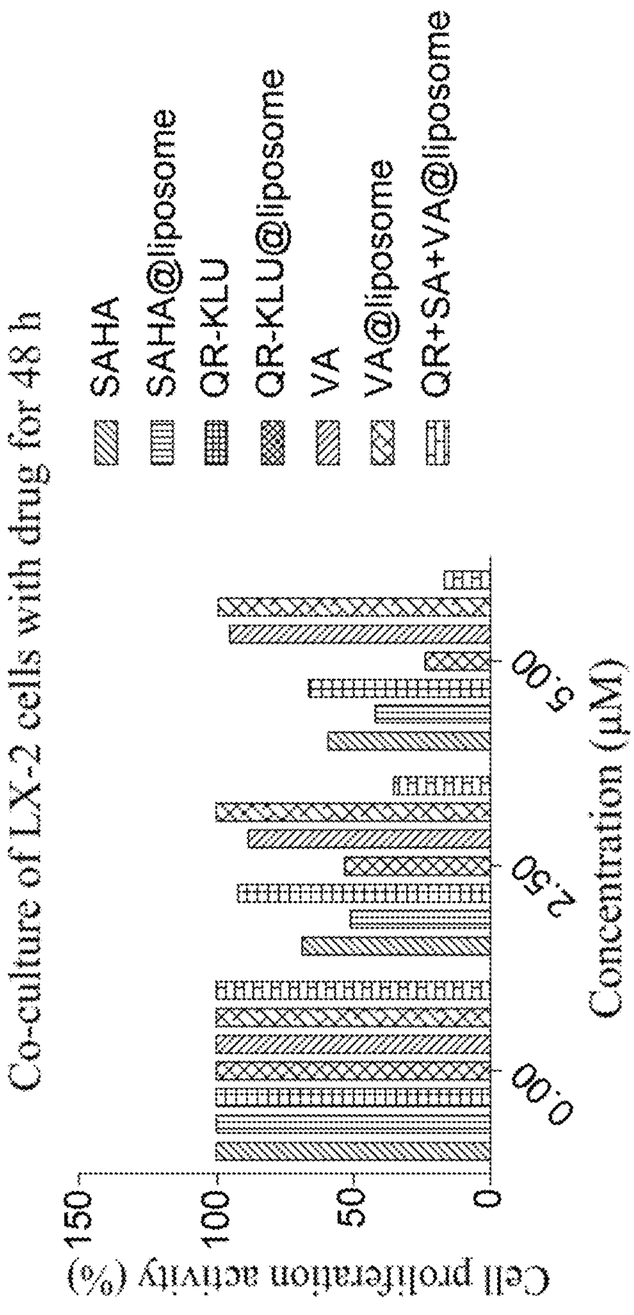
FIG. 3 is a diagram showing an influence of the relevant components of the liposome in Example 3 on the proliferation activity of LX-2 cells (normal human HSC line)

3. The experimental results were shown in FIG. 3. As shown in FIG. 3, the components that had a significant inhibitory effect on LX-2 cells proliferation included: SAHA, SAHA@liposome, QR-KLU@liposome, QR+SA+VA@liposome, and QR-KLU (5.0 μM); and the components that had no inhibitory effect on LX-2 cells included: VA, VA@liposome, and QR-KLU (2.5 μM).

4. Conclusion for the Experiment:

i) The drug components that had a significant inhibitory effect on HSCs were SAHA and a higher concentration of QR-KLU, which reduced the cell proliferation activity to about 60% to that of the original, while VA showed almost no effect.

ii) After being encapsulated by liposomes, the inhibitory effects of SAHA and QR-KLU on HSCs were significantly enhanced, and both reduced the cell proliferation activity to 50% or below to that of the original, indicating that liposome encapsulation could enhance the inhibitory effect of drugs on HSCs.

iii) Either SAHA or QR-KLU alone had a limited inhibitory effect on LX-2 cells at both lower (2.5 μM) and higher (5.0 μM) concentrations (the cell proliferation activity was all above 50% of the original). Although an inhibitory effect of SAHA@liposome and QR-KLU@liposome on LX-2 was enhanced after liposome encapsulation, the inhibitory effect was still not as desirable as that of liposome prepared by combining QR-KLU, SAHA, and VA on HSCs (the cell proliferation activity was below 20% of the original), indicating that the combination of the components showed a better effect than a single component. This might because SAHA inhibited histone deacetylation, while QR-KLU inhibited vascular endothelial growth factor receptor pathway, thus acting on the HSCs in two ways and then ultimately amplifying the inhibitory effect.

The results were in line with expectations, and then a group with the strongest inhibitory effect, QR-KLU+SAHA+VA@liposome (QR-KLU:VA:SAHA=1:2:2), was selected to conduct subsequent animal experiments to further verify the efficacy.

II. Animal Experiment

1. Experimental purpose: by constructing an internationally recognized mouse hepatic fibrosis model (CCL4 model), administrating different concentrations of liposome drugs to the model, and detecting hepatitis and fibrosis-related indicators, to determine whether this product could improve hepatic fibrosis in mice.

2. Experimental method: C57 mice (8 weeks old) were used to construct a hepatic fibrosis model by intraperitoneal injection of CCL4 for 4 weeks, twice a week; and 100 μL of CCL4 solution diluted with corn oil at a ratio of 1:4 was injected for each time; this experimental model scheme had been proven feasible by many SCI papers. The experimental models were divided into a "control group" (no liposome anti-hepatic fibrosis drugs were injected, i.e., CCL4 group) and an "experimental group" (there was liposome anti-hepatic fibrosis drug injected). The "experimental group" was further divided into a "low-dose group" (0.5 mg/kg mouse body weight), a "medium-dose group" (2.0 mg/kg mouse body weight), and a "high-dose group" (4.0 mg/kg mouse body weight) according to the drug concentration. The drug was dissolved in PBS solution, and administered 1 d after each intraperitoneal injection of CCL4, by 200 μL/intraperitoneal injection. After the modeling was completed, the mice were euthanized, and blood, liver and other specimens were collected for relevant tests.

3. Experimental results:

i) Liposome drugs did not affect the body weight of mice, but could significantly reduce the levels of liver enzymes (ALT and AST were positively correlated with the degree of liver damage).

Figure 4A:
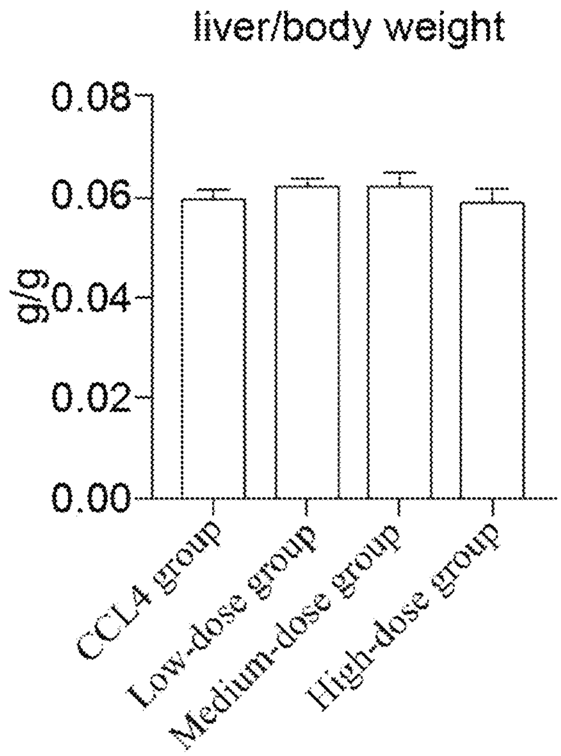
FIG. 4A-4C are diagrams showing an influence of the liposome drug in Example 3 on the body weight and liver enzyme indicators of mice (where
Figure 4B:
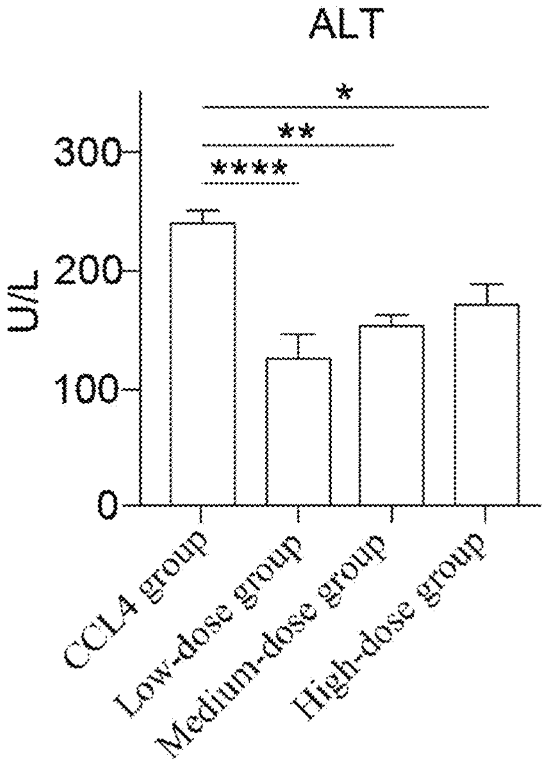
Figure 4C:
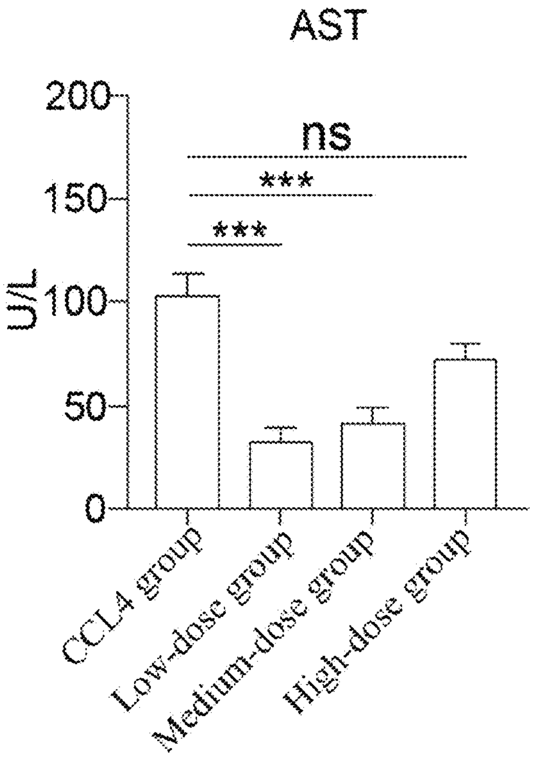

FIG. 4A-4C showed the influence of liposome drug on body weight and liver enzyme indicators of mice. Where FIG. 4A showed that there was no significant difference in the liver/body weight ratio between the "experimental group" and the "control group", indicating that the drug did not affect liver weight and body weight; FIG. 4B and FIG. 4C showed that compared with the "CCL4 group", the ALT and AST of the "medium-dose group" and the "low-dose group" had significant improvements. Although there was no statistical difference in AST in the "high-dose group", there was still an obvious downward trend, indicating that the drug could reduce damage by hepatitis from a biochemical level.

ii) The expression of genes related to inflammation (IL-1β, TNF-α) and fibrosis (α-SMA) in the experimental groups were significantly decreased.

Figure 5A:
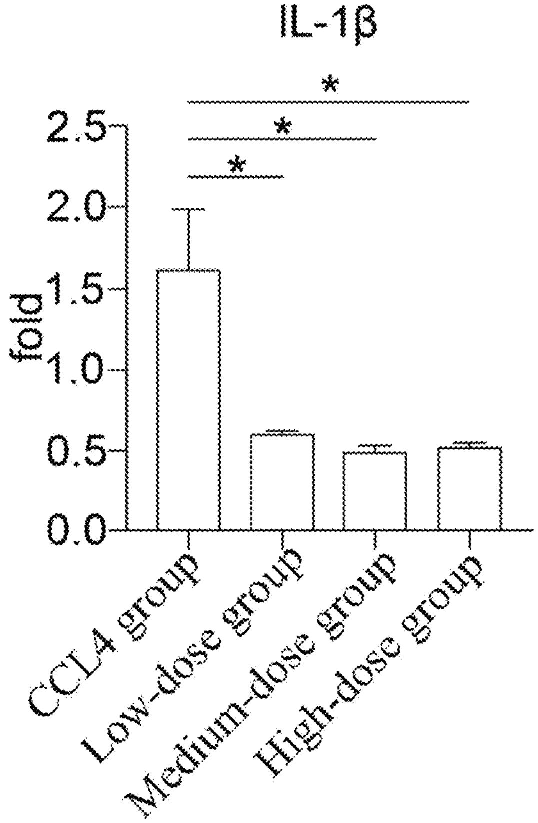
FIG. 5A-5C are diagrams showing an influence of the liposome drug in Example 3 on the expression of genes related to hepatitis and fibrosis in mice (where
Figure 5B:
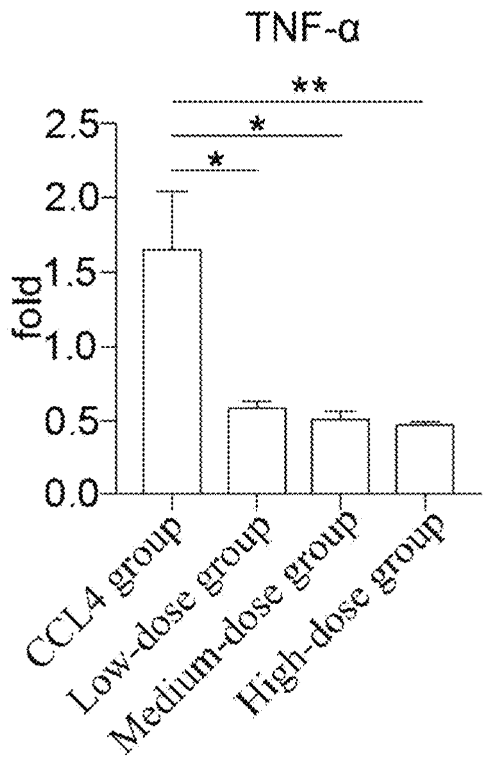
Figure 5C:
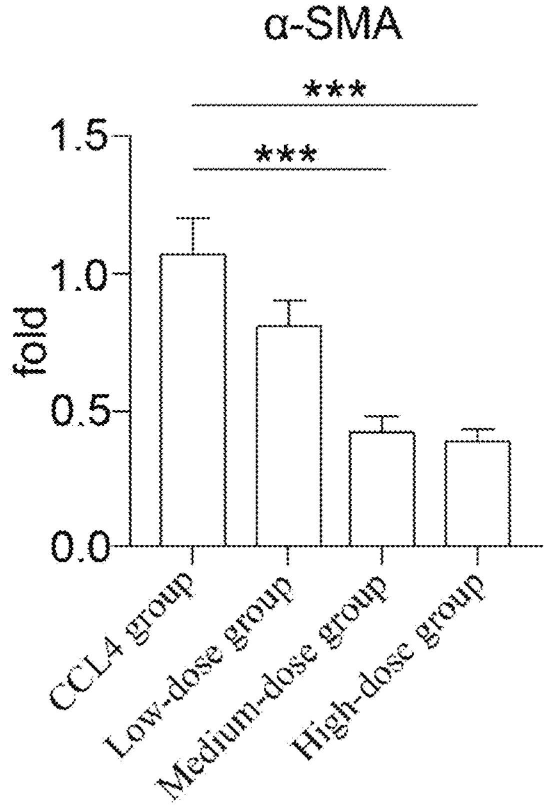

FIG. 5A-5C showed the influence of liposome drug on the expression of genes related to inflammation and fibrosis in mouse liver (where IL-1β and TNF-α were common tissue inflammatory factors, and the higher the expression level, the more severe the inflammatory damage was; α-SMA was a common indicator of hepatic fibrosis, and the higher the expression, the more collagen fibers were expressed).

As shown in FIG. 5A-5C, compared with the "CCL4 group", the indicators for hepatitis IL-1β, TNF-α (FIG. 5A to FIG. 5B) and fibrosis indicator α-SMA (FIG. 5C) decreased significantly. This indicated that the drug intervention inhibited the expression of genes related to hepatitis and hepatic fibrosis, and confirmed that the drug could reduce hepatitis and hepatic fibrosis at the transcriptome level.

iii) The inflammation of the liver tissue was significantly alleviated in the "experimental group".

Figure 6:
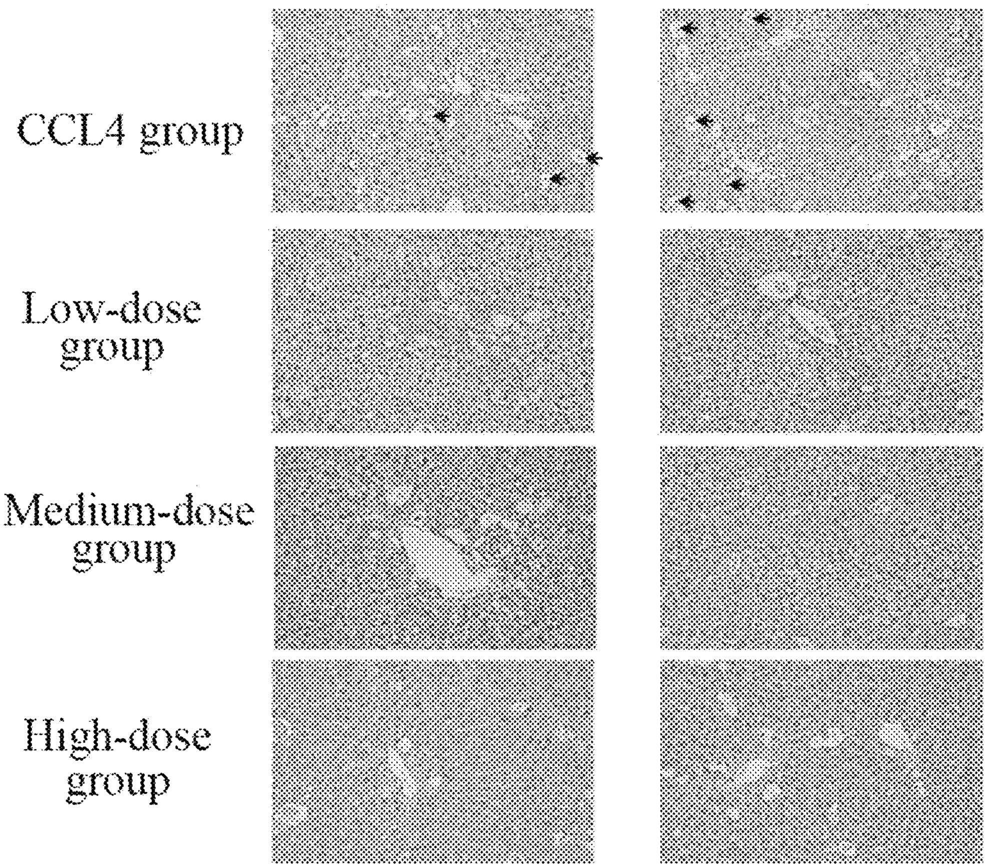
FIG. 6 shows an influence of the liposome drug in Example 3 on the inflammation in mouse liver tissue (H&E staining, magnified 100 times)

FIG. 6 showed an influence of the liposome drug on the inflammation of the liver tissue of mouse (H&E staining, magnified 100 times). A main pattern of hepatitis was determined through the distribution and composition of inflammatory cells by H&E staining of the liver. In FIG. 6, around zone 3 of the image for "CCL4 group", there was infiltration by a large number of inflammatory cells, mainly lymphocytes, and focal necrosis, ballooning degeneration on many hepatocytes and Mallory-denk bodies (indicated by arrows) can be observed. There was infiltration by a small to moderate number of inflammatory cells around a portal tract of the "experimental groups", ballooning degeneration on less hepatocytes, and fewer Mallory-denk bodies, but the degree of improvement did not present dose-related.

iv) The hepatic fibrosis in the experimental groups was alleviated significantly.

Figure 7:
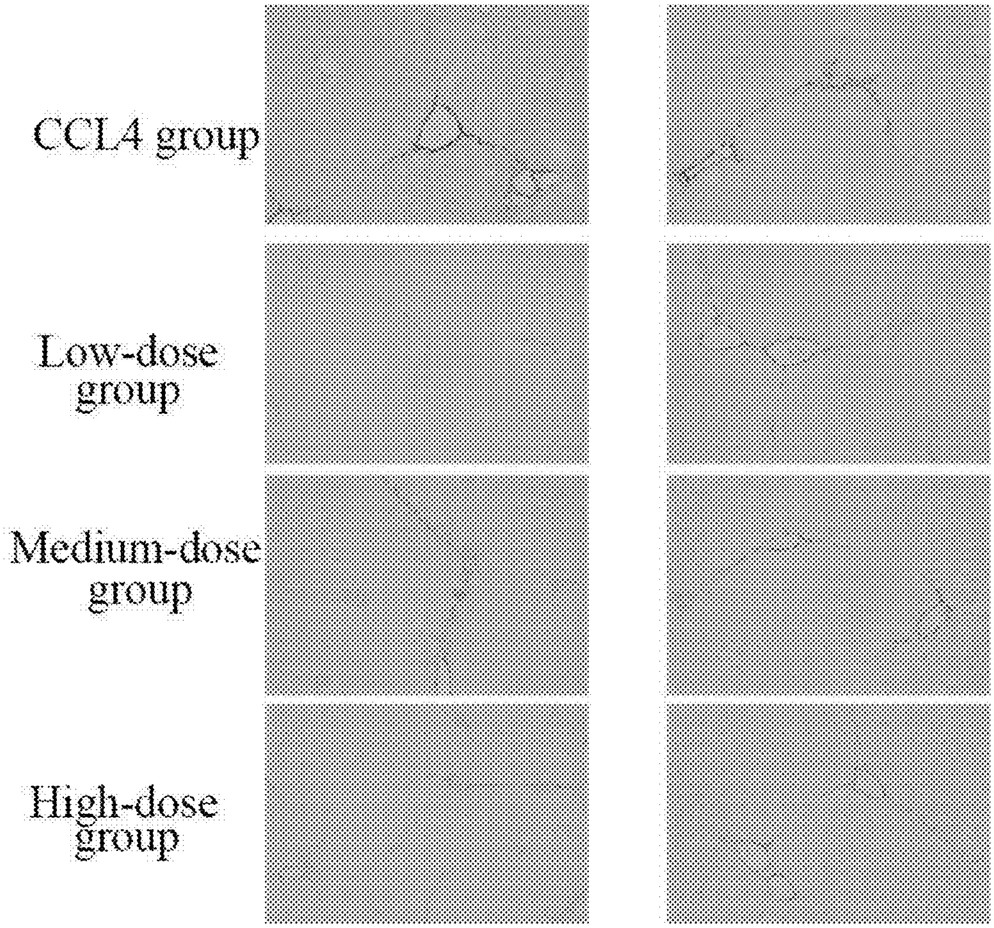
FIG. 7 shows an influence of the liposome drug in Example 3 on the liver tissue fibrosis in mice (Sirius red staining, magnified 100 times).

FIG. 7 showed an influence of the liposome drug on the liver tissue fibrosis in mice (Sirius red staining, magnified 100 times). Sirius red staining could dye collagen fibers red, while CCL4 could induce obvious hepatic fibrosis, which appeared as a red cord-like structure.

As shown in FIG. 7, the "CCL4 group" had obvious hepatic fibrosis, and the fibrous tissues were connected to the portal tract and/or central vein. The "experimental groups" all showed different degrees of hepatic fibrosis alleviation, among which the "medium-dose group" had the most significant improvement in hepatic fibrosis, with the fibrous septa almost disappearing and the stained areas significantly reduced. This indicated that the drug could improve hepatic fibrosis at the tissue level, which was consistent with the results by qPCR.

4. Conclusion of the Experiment: liposome-encapsulated anti-hepatic fibrosis drugs could significantly reduce CCL4-induced hepatic fibrosis at multiple levels, including: the liposome drugs disclosed herein could reduce the levels of biochemical indicators (ALT and AST) in the serum that reflect liver damage; at the transcriptional level, the liposome drugs could reduce the expression of the genes related to proinflammatory cytokines (IL-1β, TNF-α) and fibrosis (α-SMA). At the tissue level, the liposome drugs could allieviate inflammatory cell infiltration and ballooning degenaration of the liver, and reduce the formation of hepatic fibrosis.

The above described are merely preferred examples of the present disclosure, and are not intended to limit the present disclosure. Any modification, equivalent substitution, and improvement without departing from the spirit and principle of the present disclosure shall be included within the protection scope of the present disclosure.

What is claimed is:

1. A method for preparing a liposome encapsulating a polypeptide, suberoylanilide hydroxamic acid (SAHA), and vitamin A, comprising the following steps:

S1, dissolving choline, cholesterol, an anti-angiogenic lytic peptide, the SAHA, and the vitamin A in a chloroform-methanol solution and mixing evenly, and subjecting an obtained mixed solution to spin drying under reduced pressure to form a film; and S2, subjecting the film to hydration with a phosphate-buffered saline (PBS) solution or $ddH_2O$ to obtain the liposome;

wherein the choline, the cholesterol, the anti-angiogenic lytic peptide, the SAHA, and the vitamin A in step S1 are mixed at a molar ratio of 10:8:1:2:2.

2. The method for preparing a liposome encapsulating a polypeptide, SAHA, and vitamin A according to claim 1, wherein chloroform and methanol in the chloroform-methanol solution in step S1 are mixed at a volume ratio of 1:1.

3. The method for preparing a liposome encapsulating a polypeptide, SAHA, and vitamin A according to claim 1, wherein the liposome is used to improve hepatitis and hepatic fibrosis.

4. The method for preparing a liposome encapsulating a polypeptide, SAHA, and vitamin A according to claim 3, wherein chloroform and methanol in the chloroform-methanol solution in step S1 are mixed at a volume ratio of 1:1.

5. A method for treating hepatic fibrosis in a subject, comprising administrating a liposome prepared by the method for preparing a liposome encapsulating a polypeptide, SAHA, and vitamin A according to claim 1 to the subject in need thereof.

6. The method for treating hepatic fibrosis according to claim 5, wherein chloroform and methanol in the chloroform-methanol solution in step S1 are mixed at a volume ratio of 1:1.

7. A method for treating hepatitis in a subject, comprising administrating a liposome prepared by the method for preparing a liposome encapsulating a polypeptide, SAHA, and vitamin A according to claim 1 to the subject in need thereof.

* * * * *